United States Patent
Bunks

(10) Patent No.: US 6,240,051 B1
(45) Date of Patent: *May 29, 2001

(54) ACOUSTIC SURVEILLANCE APPARATUS AND METHOD

(75) Inventor: Carey D. Bunks, Boston, MA (US)

(73) Assignee: GTE Service Corporation, Irving, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,646

(22) Filed: Sep. 4, 1998

(51) Int. Cl.[7] .................................................. G01S 3/80
(52) U.S. Cl. ........................... 367/127; 367/129; 367/118
(58) Field of Search .................................... 367/127, 118, 367/119, 129, 124; 376/249; 73/587, 40.5 A, 657, 643, 592

(56) References Cited

U.S. PATENT DOCUMENTS

| | | | |
|---|---|---|---|
| 4,083,031 | 4/1978 | Pharo, Jr. ............................... | 340/5 R |
| 4,415,979 | * 11/1983 | Hernandez ............................ | 367/136 |
| 4,592,034 | * 5/1986 | Sachse et al. ........................ | 367/127 |
| 4,654,648 | 3/1987 | Herrington et al. .................. | 340/710 |
| 5,099,455 | 3/1992 | Parra ..................................... | 367/120 |
| 5,293,555 | 3/1994 | Anthony ............................... | 364/508 |
| 5,679,899 | * 10/1997 | Webster et al. ....................... | 73/657 |
| 5,754,497 | * 5/1998 | Tapia-Egoavil ...................... | 367/127 |

OTHER PUBLICATIONS

Dye, Lee, Press Release "Invention More than a Blip on the Radar Screen," www.ABCNEWS.com.

* cited by examiner

Primary Examiner—Ian J. Lobo
(74) Attorney, Agent, or Firm—Leonard Charles Suchyta; James K. Weixel; Floyd E. Anderson

(57) ABSTRACT

An apparatus and method for detecting, locating, tracking, or classifying an acoustic energy source located on a far side of a structure is disclosed. In accordance with the present invention, a receiving device samples a plurality of points on a near side of the structure to detect vibrations that result from sound waves propagated by the acoustic energy source. The location of the acoustic energy source is determined based on the relative time differences of the vibrations and the known positions of the vibrations on the structure. The acoustic energy source may be classified based on identifying characteristics of the vibrations. In addition, a device may be provided to transmit a sound wave through the structure. The receiving devices samples a plurality of points on the near side of the structure to detect vibrations resulting from reflections of the sound wave from the object.

17 Claims, 8 Drawing Sheets

ACOUSTIC SURVEILLANCE APPARATUS AND METHOD

BACKGROUND OF THE INVENTION

The present invention relates generally to surveillance devices. More particularly, the invention relates to an apparatus and a method for passive or active acoustic surveillance.

There are many situations in which surveillance devices, or other devices that are capable of providing information about the location and movement of people, are valuable tools. One exemplary situation occurs when rescuers are attempting to locate disaster victims. Other examples include criminal or terrorist situations where hostages have been taken or where police must enter a building in which an armed or dangerous suspect may be hiding. These types of situations present dangerous scenarios for both the hostages and the police or other law-enforcement agents who are responsible for handling the situation. The danger arises, in large part, because the law enforcement agents typically cannot detect with certainty the number and location of individuals within the building. In addition, the law enforcement agents often cannot detect a precise location of particular individuals, such as suspects, within the building thus complicating the agents' ability to resolve the situation.

Therefore, surveillance devices capable of providing detailed information about the number, location, and movement of the individuals within the building can aid the law enforcement agents in making tactical decisions in these types of situations. If the agents are able to monitor the location and movement of those inside the building, the agents make better decisions on how to resolve the situation quickly and safely.

Most surveillance devices operate on a line of sight principle, requiring visual detection of individuals. However, if a clear view into the building is not available, the law enforcement agents must resort to other types of surveillance methods to gather information about the number, location, and movements of the individuals within the building. A surveillance device using radar signals to locate and track people within the building is one possibility. However, radar signals do not travel well through metal. Thus, if the building contains metal structures, as often occurs, the information provided by the radar surveillance may not be capable of detecting individuals in the building with a reasonable degree of accuracy.

In light of the foregoing there is a need for a method and device for providing surveillance information about sources of acoustic energy positioned behind a structure.

SUMMARY OF THE INVENTION

The present invention is directed to a method and apparatus for detecting an acoustic energy source located on a far side of a structure.

A first method consistent with the present invention involves sampling a plurality of points on a near side of the structure to detect the vibrations that result from the propagation of sound waves from the acoustic energy source through the structure. The relative elapsed time differences between detection of the vibrations is measured. Based upon the measured time differences and the known positions of the sampled points on the structure, an estimate of the position of the acoustic energy source with respect to the structure can be determined.

A second method consistent with the present invention includes transmitting a sound wave through the structure from a near side of the structure and sampling a plurality of points on the near side of the structure to detect vibrations resulting from reflections of the sound wave from the object on the far side of the structure.

A third method consistent with the present invention includes tracking and classifying an acoustic energy source located on a far side of a structure. The method includes sampling a plurality of points on a near side of the structure to detect vibrations that result from the propagation of sound waves from the acoustic energy source through the structure. The acoustic energy source is classified based upon identifying characteristics of the vibrations.

An apparatus consistent with the present invention detects an acoustic energy source located on a far side of a structure. The apparatus includes a receiving device for sampling a plurality of points on a near side of the structure to detect vibrations resulting from propagation of sound waves from the acoustic energy source through the structure. A device is coupled to the input device for measuring relative elapsed time differences in detection of the vibrations. The device also determines an estimate of a position of the acoustic energy source with respect to the structure based upon known positions of the sampled points on the structure and the measured time differences.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DETAILED DESCRIPTION

Reference will now be made in detail to embodiments of the invention, examples of which are illustrated in the accompanying drawings. Wherever possible, the same reference numbers will be used throughout the drawings to refer to the same or like parts.

In accordance with the present invention, a method and apparatus for detecting an acoustic energy source located on a far side of a structure is provided. An exemplary embodiment consistent with the present invention is illustrated in FIG. 1 and is generally designated by the reference number 10.

Figure 1:
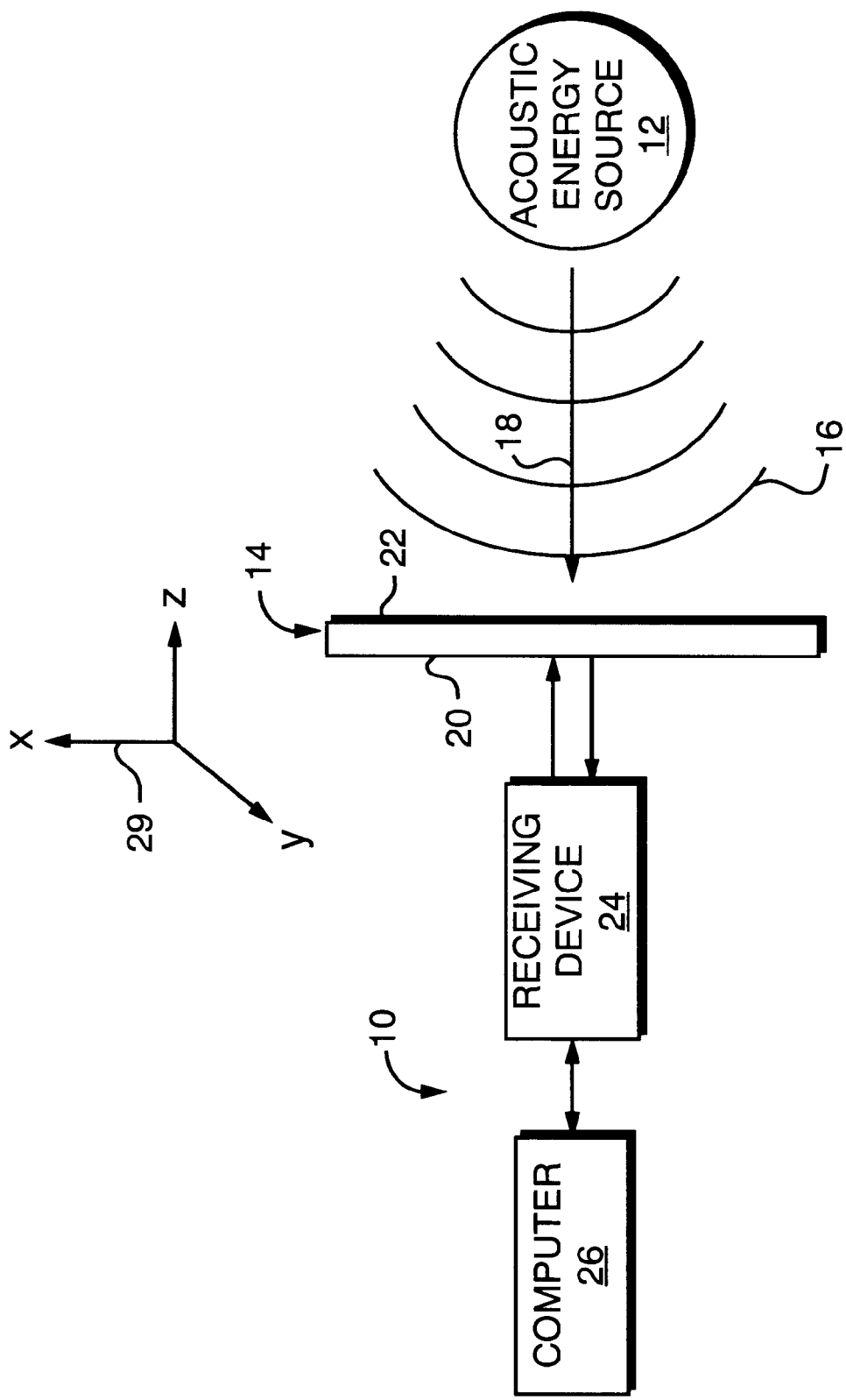
FIG. 1 is a block diagram of an apparatus for detecting a sound wave generated by an acoustic energy source positioned on the opposite side of a structure.

As illustrated in FIG. 1, the apparatus 10 of the present invention is positioned on the opposite side of a structure 14 from an acoustic energy source 12. In the illustrated embodiment, structure 14 is a wall having a near side 20 and a far side 22. Structure 14 may be any structure, natural or man-made, through which a sound wave may propagate.

As shown in FIG. 1, acoustic energy source 12 generates a sound wave 16. Acoustic energy source 12 may be any source of acoustic energy that is capable of producing a sound wave. Examples include, but are not limited to, a human voice, a heart beat, or any sound produced through movement by an individual.

Figure 2:
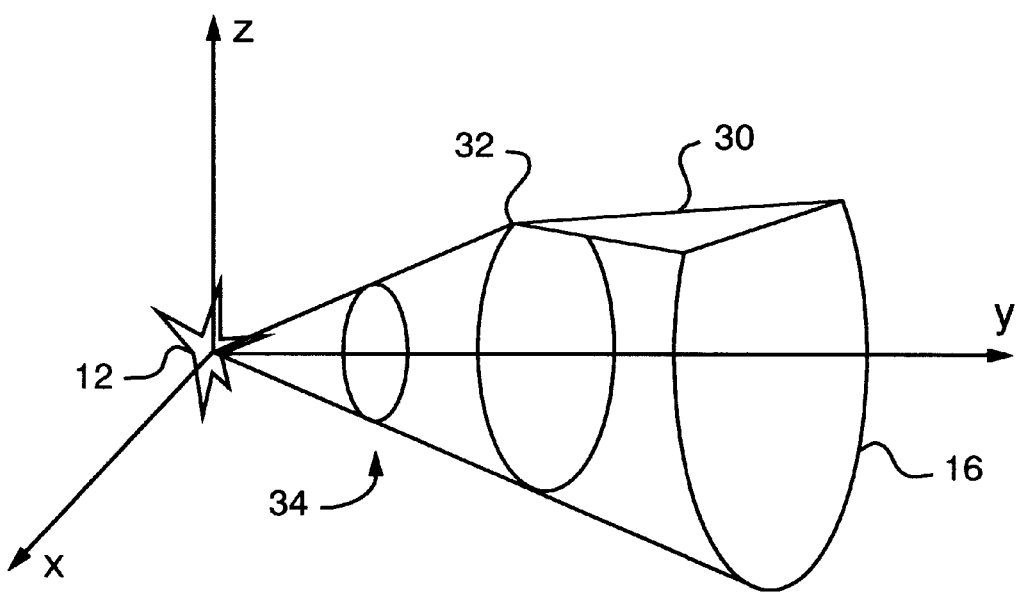
FIG. 2 is a graph representing a sound wave propagating from an acoustic energy source in two dimensions as a function of time.

As indicated by arrow 18, sound wave 16 propagates away from acoustic energy source 12 and towards far side 22 of structure 14. As understood by one skilled in the art, sound wave 16 propagates outwardly from acoustic energy source 12 in the x, y, and z directions as a function of time. As shown by axis 29, the z coordinate describes the distance from structure 14 to acoustic energy source 12 and the x and y coordinates describe a location on structure 14. FIG. 2 illustrates the propagation of sound wave 16 in the x and z directions as a function of time. As shown, the resulting surface in the space-time graph is a cone 34.

Sound wave 16 continues to expand as cone 34 until reaching far side 22 of structure 14. As shown in FIG. 2, if sound wave 16 is observed at some positive z distance from the location of acoustic energy source 12, the result will be a planar cut 30 at the distance z from acoustic energy source 12. As shown in FIG. 1, structure 14 serves as the observation point located at z distance from acoustic energy source 12. Thus, the intersection of sound wave 16 and structure 14 results in the planar cut 30 (referring to FIG. 2) that has a hyperbolic shape with an apex 32.

As the sound wave impinges on far side 22 of structure 14, the sound wave 16 will cause vibrations to propagate through the structure 14 to near side 20. The vibrations will appear on near side 20 of structure 14 with approximately the same shape and relative elapsed time difference as the sound wave 16 impinges on far side 22 of structure 14.

A receiving device 24, operating under control of computer 26, samples a plurality of points on a near side of the structure to detect vibrations resulting from propagation of sound waves from the acoustic energy source through the structure. Receiving device 24 samples the points on the structure in a particular pattern, which may be predetermined and possibly changed based upon received signals.

In one embodiment, receiving device 24 is a scanning laser vibrometer. However, any instrument readily apparent to one skilled in the art as being capable of detecting vibrations on near side 20 of structure 14 may be used. For example, commonly known and readily apparent instruments such as laser vibrometers, microphones, lasers, accelerometers, or geophones may used to detect vibrations propagating to near side 20 of structure 14.

As shown in FIG. 1, receiving device 24 is positioned on the near side 20 of structure 14. The position of receiving device 24, with respect to structure 14 depends on the operating nature of the instrument selected to operate as the receiving device 24. For example, instruments such as accelerometers or the like should be placed directly on the near side of the structure to detect vibrations. However, instruments such as laser vibrometers or the like should be positioned at some point removed from the near side of the structure. The optimal placement for any instrument capable of operating as receiving device 24 will be readily apparent to one skilled in the art.

A device, such as computer 26, measures relative elapsed time differences in detection of the vibrations. Based upon the measured time differences and the known positions of the sampled points (locations) on the structure, the device determines an estimate of a position of acoustic energy source 12 with respect to structure 14.

Figure 3:
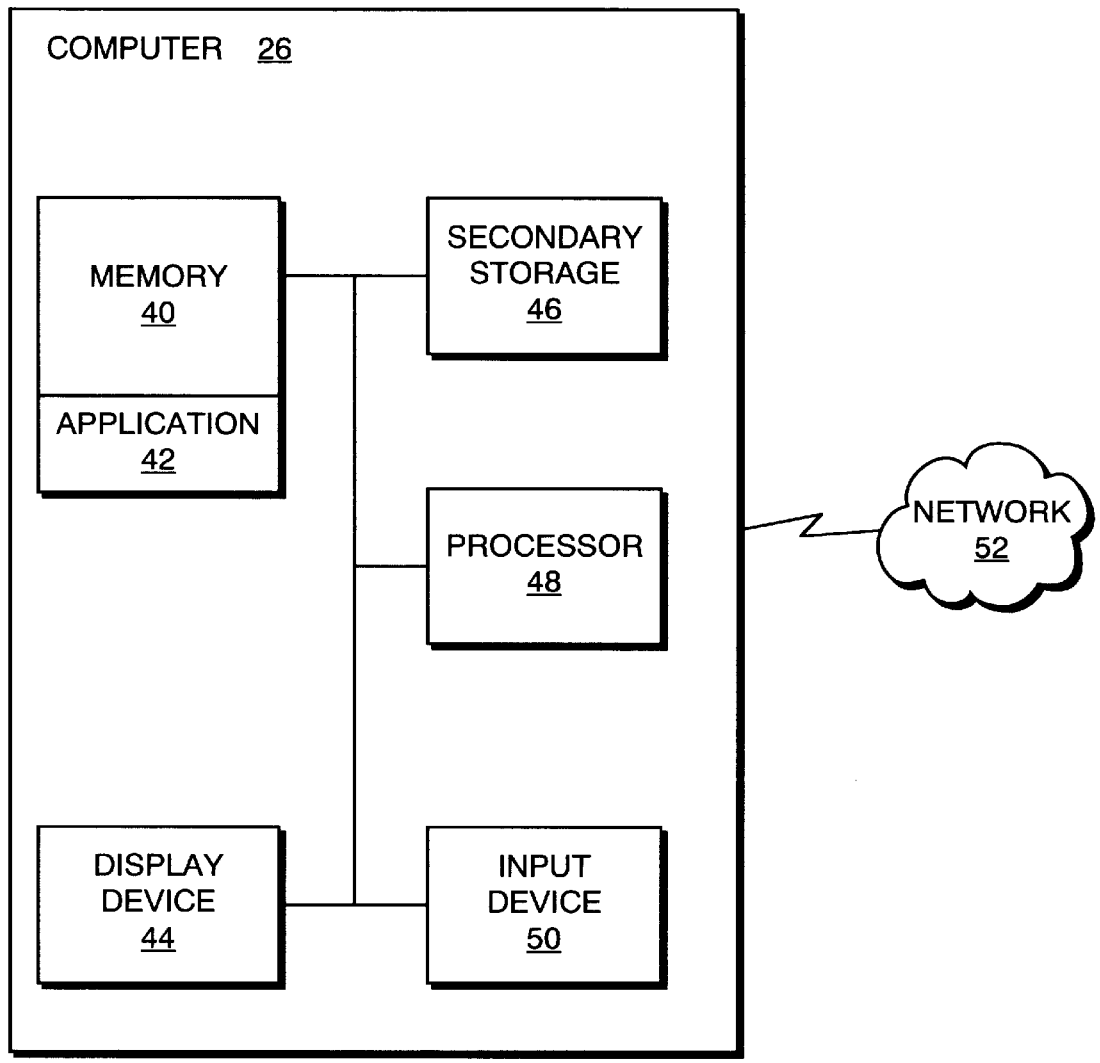
FIG. 3 is a diagram of a device for measuring the relative elapsed time difference between detection of vibrations and for determining the location of the acoustic energy source.

FIG. 3 depicts in more detail computer 26 suitable for measuring relative elapsed time differences between detection of the vibrations and for determining an estimate of a position of the acoustic energy source with respect to the structure. Computer 26 is optionally connected to a network 52, such as the Internet.

Computer 26 includes a memory 40, a secondary storage device 46, a processor 48 such as a central processing unit, an input device 50, and a display device 44. Memory 40 and secondary storage 46 may store applications, such as application 42, or information for execution and use by processor 48.

Although computer 26 is depicted with various components, one skilled in the art will appreciate that this computer can contain additional or different components. Additionally, although computer 26 is shown connected to network 52, computer 26 may be connected to other networks, including other wide area networks or local area networks. Furthermore, although aspects of the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from a network such as the Internet; or other forms of RAM or ROM. These aspects of the present invention may also include modules, implemented in software, hardware, or a combination, configured to perform a particular method implementing an embodiment consistent with the present invention. In addition, the computer-readable media may include instructions for controlling a computer system, such as computer 26, to perform a particular method.

As illustrated in FIG. 1, computer 26 is connected to receiving device 24. When receiving device 24 detects vibrations on near side 20 of structure 14, the receiving device sends the detected vibrations, or any other suitable form of communication, to computer 26 which then determines whether a target source is present, localizes its position, tracks its position, and classifies the target.

Figure 4:
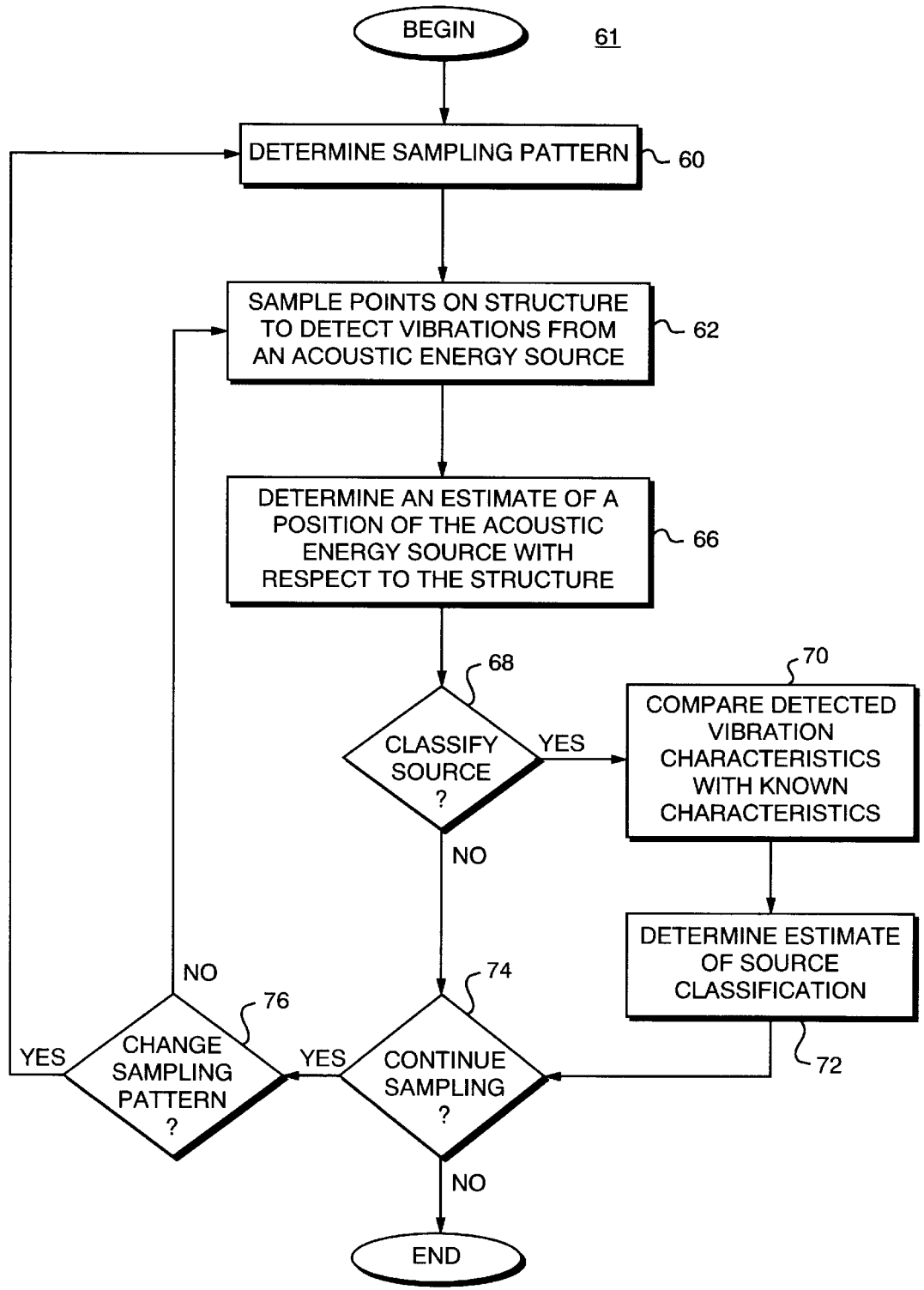
FIG. 4 is a flow chart illustrating a process for acoustic surveillance.
Figure 5:
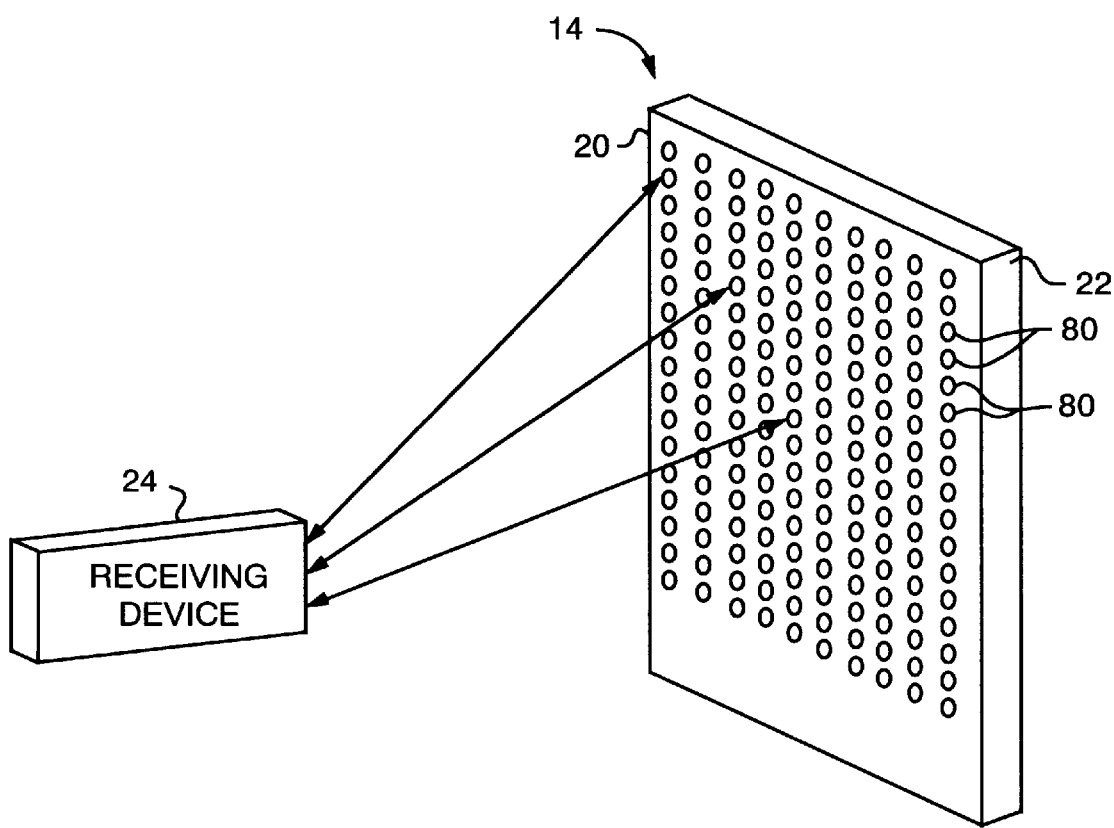
FIG. 5 is a perspective view of a receiving device and an exemplary sampling pattern on a near side of a structure.

FIG. 4 is a flow chart of an exemplary process 61 for detecting and classifying acoustic energy sources. Process 61 may be implemented by application 42 stored in memory 40 and controlling operation of processor 48. A sampling pattern is determined (step 60). Receiving device 24 samples the near side 20 of structure 14 with a particular sampling pattern. As shown in FIG. 5, the sampling pattern of receiving device 24 includes a plurality of fixed points 80 located on near side 20 of structure 14. Each point 80 is spaced a certain distance from the next point and is sampled at a particular rate.

The spacing between each point 80 and the total number of points included in the sampling pattern is based on particular criteria. The criteria includes the sampling capabilities of receiving device 24. For example, a single scanning laser vibrometer may scan a large number of points.

Accelerometers, in contrast, must be fixably mounted to the wall to sample the point.

The aperture of the sampling pattern is also dependent upon the operating nature of the receiving device. Certain instruments may be capable of sampling a large number of points over a large area of the near side of the structure, whereas other instruments may be more limiting in the area available for sampling. The aperture of the sampling pattern may also depend on the particular characteristics of the structure being sampled.

Another criteria that affects the sampling pattern of the receiving device is the transmission characteristics of the structure being sampled. If, for example, the structure, as illustrated in FIG. 1, is a wall, the optimal sampling points may be along portions of the wall backed by studs. Similar characteristics in other structures may also be used to determine the sampling pattern. Other criteria that could affect the number of points to be sampled and the distance between the sampled points will be readily apparent to one skilled in the art.

Another component of the sampling pattern includes the rate at which the receiving device samples each point on the structure. The rate of sampling each point is also based on particular criteria. The operating nature of the receiving device 24 affects the rate at which the points 28 are sampled. Certain instruments, for example the accelerometers, must be fixably mounted to near side 20 of structure 14. Thus, these types of instruments may continuously sample each designated point 28. Other instruments, such as the scanning laser vibrometer, for example, sequentially scan through the sampling pattern. Preferably, the rate at which each point is sampled is high enough that vibrations are detected soon after they appear on the near side of the structure.

After the sampling pattern has been determined, receiving device 24 samples the near side of the structure in the determined sampling pattern (step 62). As described above, after acoustic energy source 12 generates sound wave 16, the sound wave propagates towards structure 14 as a function of time.

Figure 6:
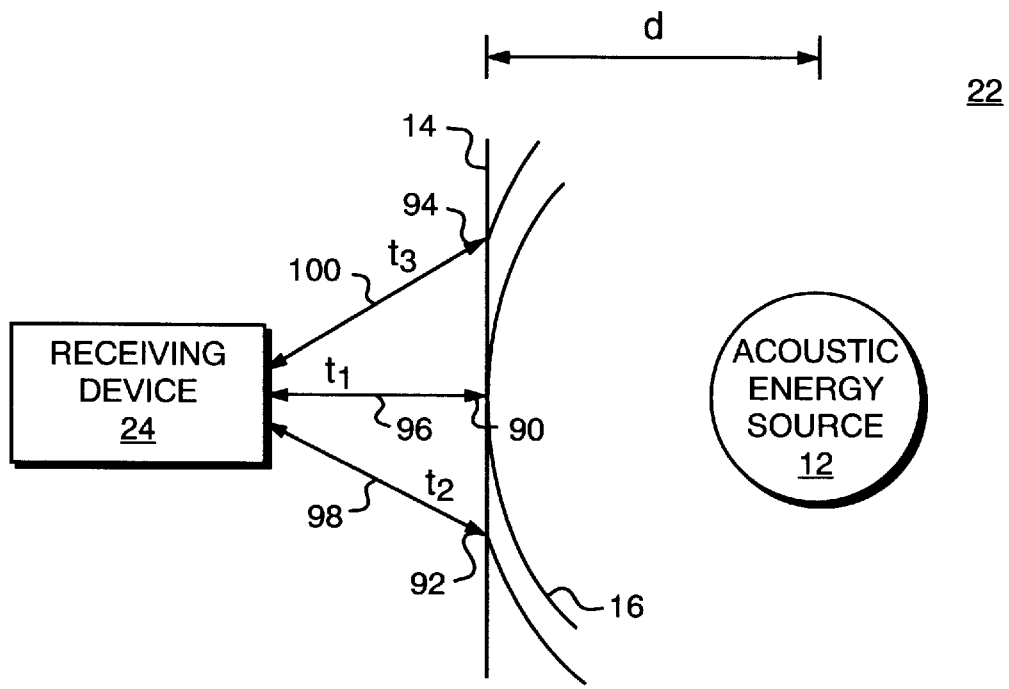
FIG. 6 is a block diagram of a receiving device for detecting vibrations on the near side of a structure as a function of time.

As shown in FIG. 6, the sound wave will first impinge the point 90 of structure 14 nearest an acoustic energy source 12. The sound wave will continue to impinge upon other points on the near side of the structure as the sound wave continues to propagate. The impingement of the sound wave on the far side of the structure causes vibrations in the structure, which travel through the structure and appear on the near side of the structure.

Receiving device 24 detects the vibrations as they appear on the near side of the structure. The first vibration, at point 90 on structure 14 nearest acoustic energy source 12 is detected at time, $t_1$, as indicated by arrow 96. As receiving device 24 samples the points on the near side of the structure, other vibrations are detected at points 92 and 94. These points appear at times $t_2$ and $t_3$ as indicated by arrows 98 and 100, respectively. The receiving device sends the detected vibration, or a similar communication, to computer 26 and identifies the location of points 90, 92, and 94 at which the vibrations were detected and computer 26 measures the time differences between the detected vibrations.

Based upon the relative location of the detected vibrations and the measured time differences, such as $t_2-t_1$ and $t_3-t_1$ as illustrated in FIG. 6, computer 26 determines, through triangulation, migration or any other appropriate techniques, an estimate of the location of acoustic energy source 12 with respect to the structure (step 66). An exemplary two-dimensional triangulation technique that may be used to determine the location of the acoustic energy source is based on the shape of cone 34 in the space-time graph of FIG. 2 formed by the expansion of sound wave 16. The shape or the cone is given by the following formula:

$$t = t_0 + \frac{1}{c}\sqrt{(x-x_0)^2 + (z-z_0)^2} \quad [1]$$

Where $t-t_0$ is the travel time of the wavefront to the point (x, z);

$t_0$ is the time at which the source is triggered;

c is the phase velocity of the sound wave; and $x_0$, $z_0$ is the spatial location of the acoustic energy source.

The source of acoustic energy may be determined if the location of the apex 32 and any other point on the hyperbola are known. At the apex 32 of hyperbola 30, $x=x_0$. Assuming that $x_0=0$ and $z_0=0$ equation [1] above becomes:

$$t_1 = t_0 + \frac{z_0}{c} \quad [2]$$

where $t_1$ is the recorded time to the apex of the hyperbola.

The following equation is for any other point on the hyperbola:

$$t_2 = t_0 + \frac{1}{c}\sqrt{x_2^2 + z_2^2} \quad [3]$$

where $t_2$ is the recorded time to the second point on the hyperbola.

Solving equations [2] and [3] for $t_0$ and $z_0$, respectively, yields:

$$t_0 = \frac{(t_2^2 - t_1^2)c^2 - x_2^2}{2(t_2 - t_1)c} \quad [4]$$

$$z_0 = c(t_1 - t_0) \quad [5]$$

The location of the apex and relative timing to the second point on the hyperbola may be used with equations [4] and [5] to determine the location of acoustic energy source 12. Application 42 may include suitable instructions for controlling processor 48 to calculate these equations. As would be readily apparent to one skilled in the art, the two-dimensional triangulation technique described herein can easily be generalized to a third dimension by similarly considering the y component of the detected vibrations.

Alternatively, the location of acoustic energy source 12 may be determined with commercially available algorithms known as migration algorithms. These migration algorithms use the basic principles set forth above and are well suited for use in the present invention because of their ability to handle parasitic waves, random noise, and modeling uncertainties. Migration algorithms are well known in the art. Migration algorithms suitable for use with the present invention are described in detail in Jenö Gazdag & Piero Sguazzero, *Migration of Seismic Data,* Proc. IEEE, 72(10):1302–1315, October 1984 and in Özdoğan Yilmaz, *Seismic Data Processing.* Society of Exploration Geophysicists, Tulsa, Okla., 1993, both of which are hereby incorporated by reference in their entirety.

Figure 7:
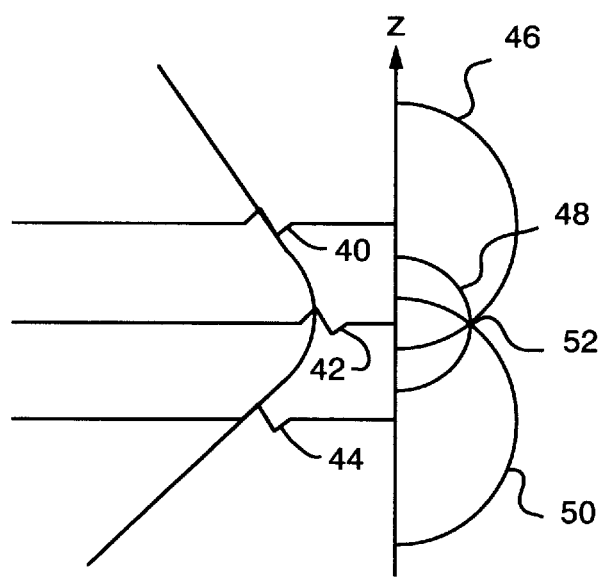
FIG. 7 is a graph of a hyperbola formed on a structure by a sound wave generated by an acoustic energy source and the corresponding back-propagated wavefronts used to estimate a position of the acoustic energy source.

The migration algorithms work by computationally back-propagating in time from detected vibrations. As illustrated in FIG. 7, three vibration points 40, 42, and 44 are detected on near surface 20 of structure 14. Each vibration point 40, 42, and 44 is treated as an acoustic energy source and a wavefront 46, 48, and 50, respectively is back-propagated from each detection point. The propagation is performed backwards in time. Since vibrations at points 40 and 44 were detected after the vibration at point 42, the back-propagated wavefronts 46 and 50 will have larger radii than back-propagated wavefront 48.

The back-propagated wavefronts 46, 48 and 50 are expanded as a function of time until all three wavefronts intersect at a certain point 52. The location at which all three circles intersect corresponds to the location at which the acoustic energy source 12 created the sound wave 16. It should be noted that back-propagating from additional vibration detection points will serve to increase the focus of the migration algorithm and will provide a more accurate location of the acoustic energy source 12.

Computer 26 is typically capable of processing the sampled vibrations to reduce noise that may be associated with the signals. Noise may be generated by vibration detections that are a result of intra-wall reverberation, room resonances, multiple arrivals off side walls, or structurally borne waves. In addition, ambient and sensor noise will act to mask the direct arrival waves. By processing the signals to reduce the noise, the accuracy of the estimated location of the acoustic energy source may be improved.

In accordance with the present invention, the acoustic energy source may be classified based on the identifying characteristics of the vibrations detected on the structure (step 68). Computer 26 may classify the acoustic energy source by comparing the detected vibration characteristics with known characteristics (steps 70 and 72) stored, for example, in memory 40 or secondary storage 46. In this manner, sounds having distinctive characteristics, for example a gunshot or a human voice, can be classified. Devices and techniques capable of comparing sounds in accordance with this aspect of the invention, such as Neural Networks or Hidden Markov Networks for example, will be readily apparent to one skilled in the art.

In addition, acoustic energy source 12 may be classified based on the movement of the detected acoustic energy source. In certain situations, the movement of the acoustic energy source provides an indication as to the nature of the acoustic energy source. For example, in a hostage situation, it might be expected that the hostages would remain stationary and the hostage takers more apt to engage in movement behind the structure. Based on the movements of the detected acoustic energy sources, the sources may be classified accordingly. The present invention contemplates that the acoustic energy source may be classified on the basis of other characteristics of the detected vibrations that are readily apparent to one skilled in the art.

After an estimate of the position of the acoustic energy source is determined and the energy source classified, the receiving device may either continue the sampling of the structure or stop the sampling of the structure (step 74). If the sampling of the structure is continued, as shown in FIG. 4, the receiving device may change the sampling pattern (step 76) to optimize the sampling pattern based upon received measurements of the vibrations. This optimization could include increasing the number of points sampled or changing the sequence of sampling or the distance between the points to better detect the vibrations. In addition, the rate at which the points are sampled may also be modified.

It is contemplated that the information regarding the classification and movement of an acoustic energy source gathered with the device of the present invention can be used with a graphical user interface displayed on display device 44. Preferably, display device 44 provides an illustration of the location, movement, and classification of each detected acoustic energy source.

Figure 9:
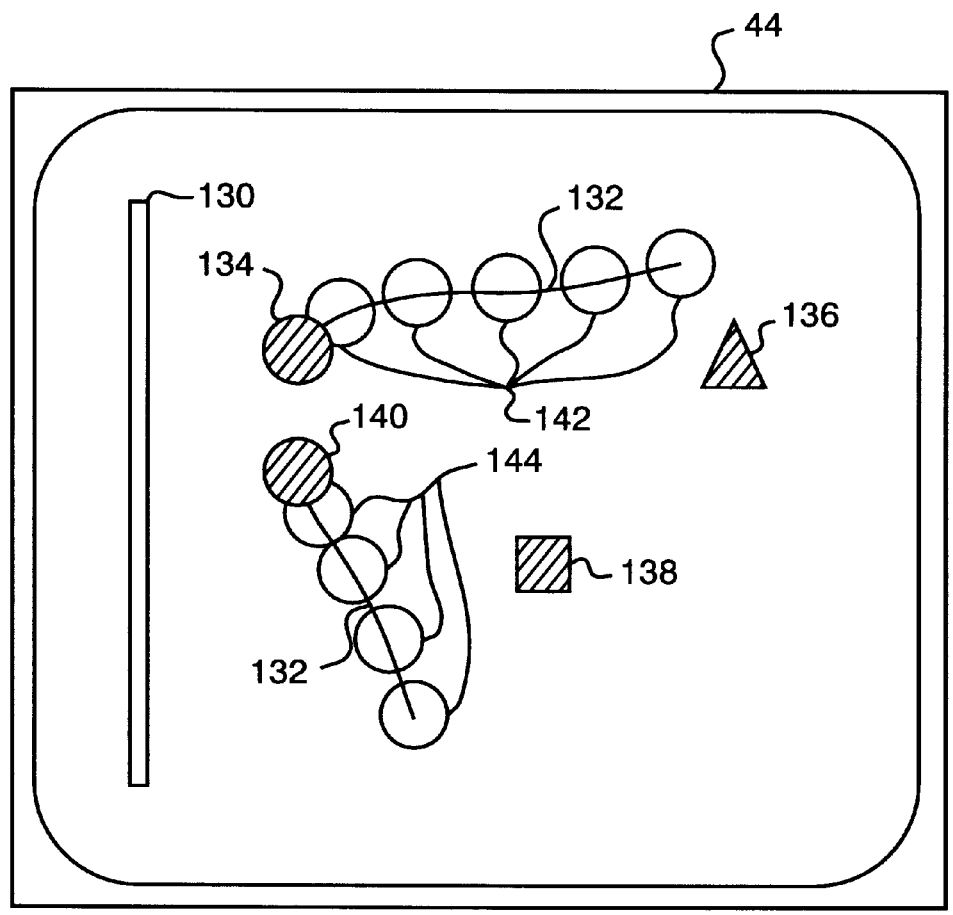
FIG. 9 is a front view of a display device displaying an exemplary graphical user interface.

As illustrated in FIG. 9, the user interface includes a representation of the structure 130 being sampled and the relative locations of detected acoustic energy sources 134, 136, 138, and 140. Preferably, the classification of the detected energy sources is identified by the shape used to represent the particular acoustic energy source, although other alternatives, for example varying the color of the display, will be readily apparent to one skilled in the art. In the illustrated example, circles 134 and 140 identify acoustic energy sources producing sounds or having movement patterns that are consistent with humans. Triangle 136 identifies the location of a machine that is producing a recognized sound. Square 138 identifies the location of an unrecognized sound. The tracked movements of detected acoustic energy sources 134 and 140 are illustrated by lines 132. The most recently detected position of each acoustic energy source is indicated by solid circles 134 and 140 and previous locations of the acoustic energy source are indicated by hollow circles 142 and 144, respectively.

Figure 8:
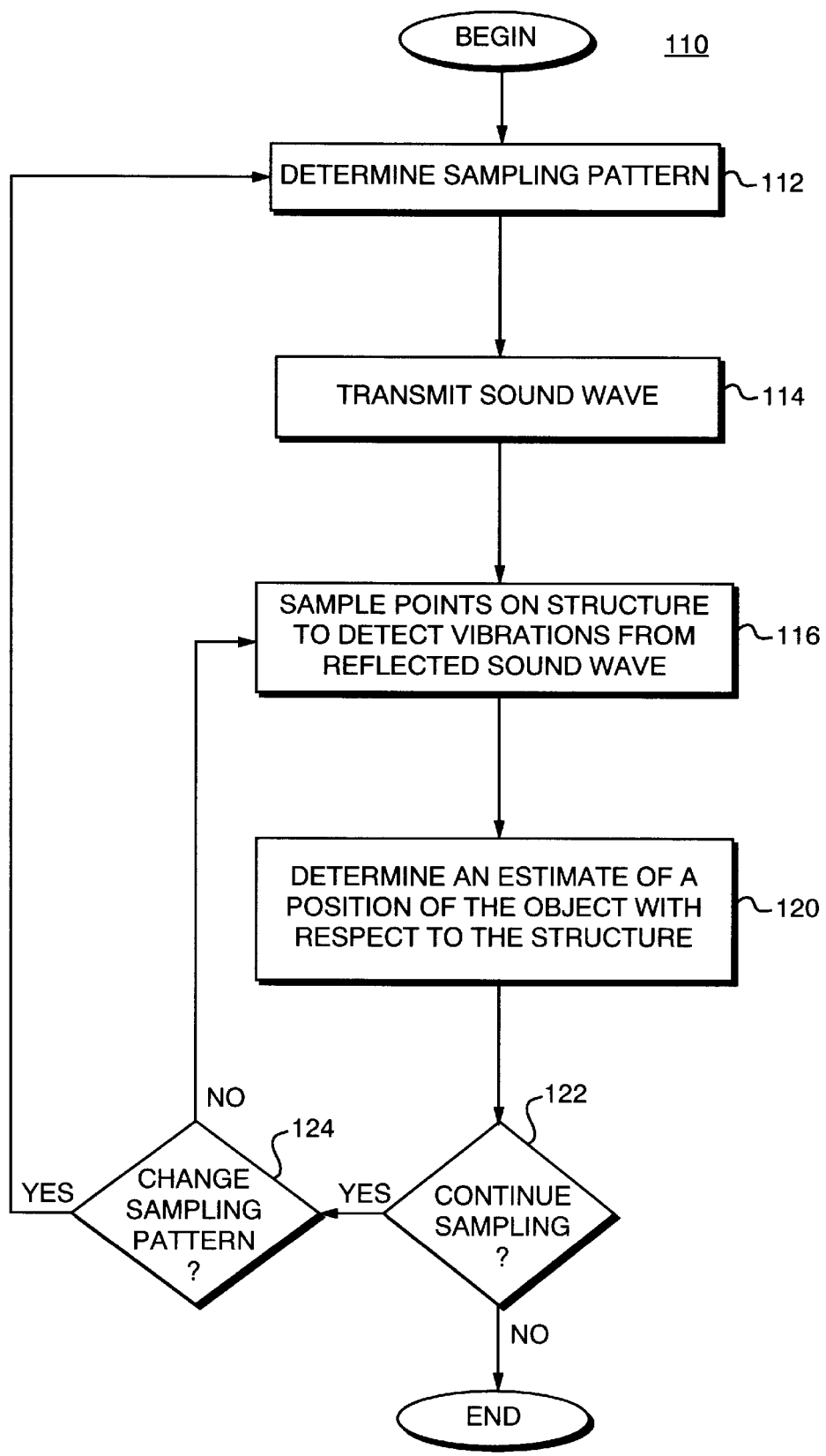
FIG. 8 is a flow chart illustrating an alternative process for acoustic surveillance.

FIG. 8 is a flow chart of an exemplary process 110 for detecting an object located on a far side of a structure. Process 110 may be implemented by application 42 stored in memory 40 and controlling operation of processor 48. As described above, a sampling pattern is determined (step 112).

A sound wave is transmitted (step 114). The sound wave is generated on the near side of the structure. The sound wave is transmitted through the structure. The transmitted sound wave reflects off of the object located on the far side of the structure.

The transmitted sound wave is reflected by the object back towards the structure. The transmitted sound wave thus operates to make the object appear as if it were an acoustic energy source that generated a sound wave. The reflected sound wave propagates back toward the structure until it impinges on the far side of the structure. The impingement of the reflected sound wave on the structure causes vibrations to propagate through the structure to the near side.

As described above, the receiving device samples the near side of the structure to detect the vibrations (step 116). The relative elapsed time differences between the detected vibrations is measured and an estimate of a position of the object is determined (steps 120). After the estimate of the position of the object is determined, the receiving device may either continue sampling the structure or stop sampling the structure (step 122). If the sampling is continued, the sampling pattern may be modified (step 124) to adapt to the present circumstances.

It will be apparent to those skilled in the art that various modifications and variations can be made in the method of detecting the acoustic energy source and the construction of the apparatus for detecting and acoustic energy source without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. A method of locating an acoustic energy source generating sound waves and located on a far side of a structure and wherein said acoustic energy source is located a distance away from the far side of the structure, the method comprising:

sampling a plurality of locations using a plurality of sensors on a near side of the structure to detect vibrations resulting from propagation of sound waves from the acoustic energy source through the structure;

measuring relative elapsed time differences in detection of the vibrations; and determining an estimate of a position of the acoustic energy source with respect to the far side of the structure based upon known positions of the sampled locations on the structure and the measured time differences.

2. The method of claim 1, wherein the sampling includes detecting vibrations radiating from the structure.

3. The method of claim 1, wherein the sampling includes using at least one of the following to sample the locations: a scanning laser vibrometer, a plurality of laser vibrometers, a plurality of microphones, a plurality of lasers, a plurality of accelerometers, or a plurality of geophones.

4. The method of claim 1, wherein the sampling includes determining a sampling pattern based upon particular criteria.

5. The method of claim 4, wherein the sampling includes determining an optimal sampling pattern based upon received measurements of the vibrations.

6. The method of claim 4 wherein the sampling includes determining the sampling pattern based upon transmission characteristics of the structure.

7. The method of claim 1, wherein the sampling includes determining a number of the points to sample based upon particular criteria.

8. The method of claim 7, wherein the sampling includes determining the distance between each of the number of sampled locations based upon particular criteria.

9. The method of claim 1, wherein the plurality of locations are sampled sequentially based upon particular criteria.

10. The method of claim 1, wherein each of the plurality of locations are sampled continuously.

11. The method of claim 1, wherein the sampling includes determining an aperture of the sampled locations based upon particular criteria.

12. The method of claim 1, wherein the determining includes triangulating the detected vibrations based on the relative elapsed time differences.

13. The method of claim 1, wherein the determining includes processing the sampled vibrations to minimize effects of noise.

14. The method of claim 1, further including the step of displaying within a user interface a visual representation of a relative location of the acoustic energy source with respect to the structure.

15. A method of locating an object located a distance away from and located on a far side of the structure, the method comprising:

transmitting a sound wave through the structure from a near side of the structure;

sampling a plurality of locations on the near side of the structure to detect vibrations resulting from reflections of the sound wave from the object through the structure;

measuring relative elapsed time differences in detection of the vibrations; and determining an estimate of a position of the object with respect to the far side of the structure based upon known positions of the sampled locations on the structure and the measured time differences.

16. An apparatus for locating an acoustic energy source located a distance away from and located on a far side of a structure, the apparatus comprising:

a receiving device for sampling a plurality of locations on a near side of the structure to detect vibrations resulting from propagation of sound waves from the acoustic energy source through the structure; and a device, coupled to the input device, for measuring relative elapsed time differences in detection of the vibrations and for determining an estimate of a position of the acoustic energy source with respect to the far side of the structure based upon known positions of the sampled locations on the structure and the measured time differences.

17. The apparatus of claim 16, wherein the receiving device includes at least one of the following to sample the points: a scanning laser vibrometer, a plurality of microphones, a plurality of lasers, an accelerometer, or a geophone.

* * * * *